(12) United States Patent
Zhu et al.

(10) Patent No.: US 8,502,971 B2
(45) Date of Patent: Aug. 6, 2013

(54) METHOD FOR DETECTING SINGLE MOLECULE

(75) Inventors: Zhen-Dong Zhu, Beijing (CN); Qun-Qing Li, Beijing (CN); Li-Hui Zhang, Beijing (CN); Mo Chen, Beijing (CN)

(73) Assignees: Tsinghua University, Beijing (CN); Hon Hai Precision Industry Co., Ltd., New Taipei (TW)

( * ) Notice: Subject to any disclaimer, the term of this patent is extended or adjusted under 35 U.S.C. 154(b) by 29 days.

(21) Appl. No.: 13/092,144

(22) Filed: Apr. 21, 2011

(65) Prior Publication Data
US 2012/0170033 A1  Jul. 5, 2012

(51) Int. Cl.
| | |
|---|---|
| G01J 3/44 | (2006.01) |
| G01N 15/06 | (2006.01) |
| G01N 21/00 | (2006.01) |
| C12Q 1/00 | (2006.01) |
| C12M 3/00 | (2006.01) |
| C12P 19/34 | (2006.01) |

(52) U.S. Cl.
USPC .......... 356/301; 422/68.1; 422/82.05; 435/4; 435/287.2; 435/91.1

(58) Field of Classification Search
USPC ........................................ 356/301, 244–246
See application file for complete search history.

(56) References Cited

U.S. PATENT DOCUMENTS

| | | | | |
|---|---|---|---|---|
| 5,891,351 A | * | 4/1999 | Lee et al. ...................... | 216/74 |
| 7,267,948 B2 | * | 9/2007 | Vo-Dinh ...................... | 435/6.11 |
| 7,483,130 B2 | * | 1/2009 | Baumberg et al. ............ | 356/301 |
| 7,741,664 B2 | * | 6/2010 | Choi et al. .................... | 257/291 |
| 7,744,816 B2 | | 6/2010 | Su et al. | |
| 7,965,388 B2 | * | 6/2011 | Xia et al. ...................... | 356/301 |
| 2006/0002656 A1 | * | 1/2006 | Cowan et al. ................. | 385/31 |
| 2008/0242556 A1 | | 10/2008 | Cao et al. | |
| 2010/0256016 A1 | * | 10/2010 | Blair et al. ..................... | 506/13 |
| 2011/0293884 A1 | * | 12/2011 | Zhu et al. ...................... | 428/119 |
| 2012/0178181 A1 | * | 7/2012 | Barhoumi et al. ............ | 436/501 |

FOREIGN PATENT DOCUMENTS

| | | | |
|---|---|---|---|
| CN | 1860370 | | 11/2006 |
| CN | 10184855.6 | * | 5/2010 |
| CN | 101765462 | | 6/2010 |

OTHER PUBLICATIONS

W. A. Murray, S. Astilean, and W. L. Barnes, "Transition from localized surface plasmon resonance to extended surface plasmon-polariton as metallic nanoparticles merge to form a periodic hole array," Physical Review B 69, 165407 (2004), hereinafter Murray.*
S. Y. Chou, P. R. Krauss, and P. J. Renstrom "Nanoimprint lithography," Journal of Vacuum Science & Technology B 14, 4129-4133 (2004), hereinafter Chou.*

* cited by examiner

*Primary Examiner* — Tarifur Chowdhury
*Assistant Examiner* — Sunghee Y Gray
(74) *Attorney, Agent, or Firm* — Altis Law Group, Inc.

(57) ABSTRACT

A method for detecting single molecule includes providing a carrier. The carrier includes a substrate and a metal layer. The substrate has a surface and defines a number of blind holes caved in the substrate from the surface thereof. The metal layer covers the surface of the substrate and inner surfaces of the number of blind holes. Single molecule samples are disposed on the metal layer. The single molecule samples are detected by a Raman Spectroscopy system.

19 Claims, 16 Drawing Sheets

US 8,502,971 B2

METHOD FOR DETECTING SINGLE MOLECULE

CROSS-REFERENCE TO RELATED APPLICATIONS

This application claims all benefits accruing under 35 U.S.C. §119 from China Patent Application No. 201010619663.3, filed on Dec. 31, 2010 in the China Intellectual Property Office, the disclosure of which is incorporated herein by reference. This application is related to applications entitled, "CARRIER FOR SINGLE MOLECULE DETECTION", filed on Apr. 21, 2011 with U.S. patent application Ser. No. 13/091,125.

BACKGROUND

1. Technical Field

The present disclosure relates to a carrier for single molecule detection, a method for making the same, and a method for using the same to detect single molecules.

2. Description of Related Art

Raman spectroscopy is widely used for single molecule detection.

A method for detecting single molecules using Raman spectroscopy is provided. An aggregated silver particle film is coated on a surface of a glass substrate. A number of single molecule samples are disposed on the aggregated silver particle film. A laser irradiation is supplied to the single molecule samples by a Raman detection system to cause a Raman scattering and produce a Raman spectroscopy. The Raman spectroscopy is received by a sensor and analyzed by a computer. However, the surface of the glass substrate is usually smooth. Thus, the Raman scattering signal is not strong enough and the resolution of the single molecule is relatively low. Therefore, the glass substrate coated with aggregated silver particle film is not suitable for detecting low concentration single molecule samples.

What is needed, therefore, is to provide a carrier for low concentration single molecule detection, a method for making the same, and a method for using the same to detect single molecule.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

References will now be made to the drawings to describe, in detail, various embodiments of the present carrier for single molecule detection, a method for making the same, and a method for using the same to detect single molecule.

Figure 1:
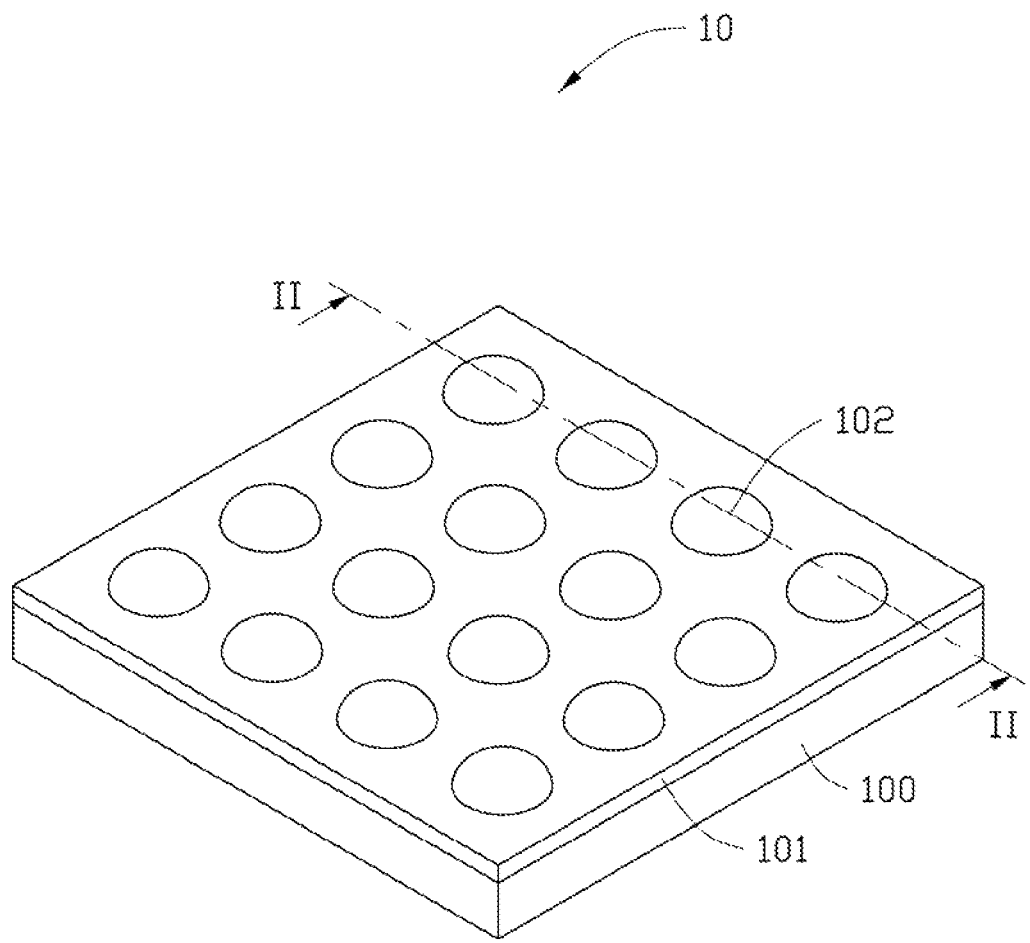
FIG. 1 is an isometric view of one embodiment of a carrier for single molecule detection.
Figure 2:
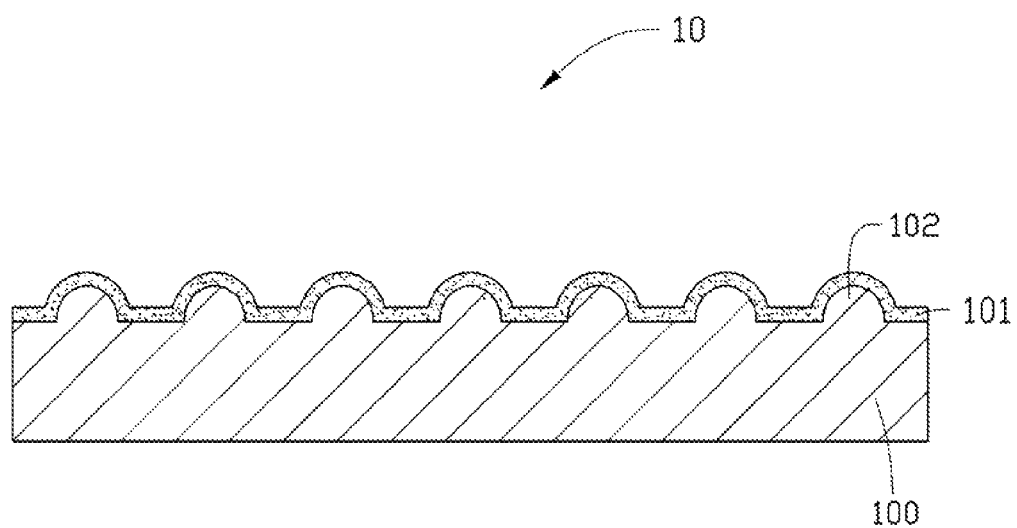
FIG. 2 is a cross-sectional view, along a line II-II of FIG. 1.

Referring to FIGS. 1 to 2, one embodiment of a carrier 10 for single molecule detection includes a substrate 100 and a metal layer 101. The substrate 100 has a surface and includes a number of three-dimensional nano-structures 102 protruding from the surface. The metal layer 101 is located on the surface of the substrate 100 and covers the three-dimensional nano-structures 102.

The substrate 100 can be an insulative substrate or a semiconductor substrate. The substrate 100 can be made of a material such as glass, quartz, silicon (Si), silicon dioxide ($SiO_2$), silicon nitride ($Si_3N_4$), gallium nitride (GaN), gallium arsenide (GaAs), alumina ($Al_2O_3$), or magnesia (MgO). The size and thickness of the substrate 100 can be determined according to need. In one embodiment, the substrate 100 is a silicon dioxide layer.

Figure 3:
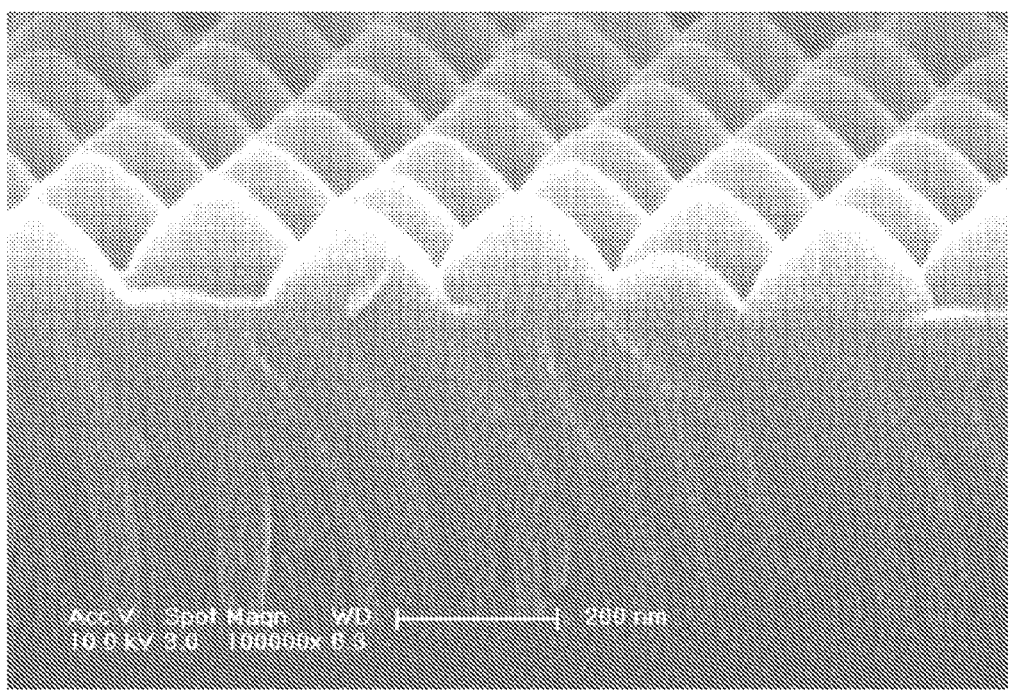
FIG. 3 is a Scanning Electron Microscope (SEM) image of a carrier for single molecule detection of FIG. 1.

Each of the three-dimensional nano-structures 102 is a bulge protruding upwardly from the surface of the substrate 100. In one embodiment, the three-dimensional nano-structure 102 is a hemispherical bulge as shown in FIG. 3. The diameter of the hemispherical bulge can be in a range from about 30 nanometers to about 1000 nanometers. In one embodiment, the diameter of the hemispherical bulge is in a range from about 50 nanometers to about 200 nanometers. The two adjacent hemispherical bulges are substantially equidistantly arranged. Two adjacent hemispherical bulges define a gap therebetween. The distance between the bottom surfaces of two adjacent hemispherical bulges can be in a range from about 0 nanometers to about 50 nanometers. If the distance is 0 nanometers, the bottom surfaces of two adjacent hemispherical bulges are in contact with each other so that the adjacent hemispherical bulges are tangent. In one embodiment, the distance between the bottom surfaces of two adjacent hemispherical bulges is about 10 nanometers.

Figure 4:
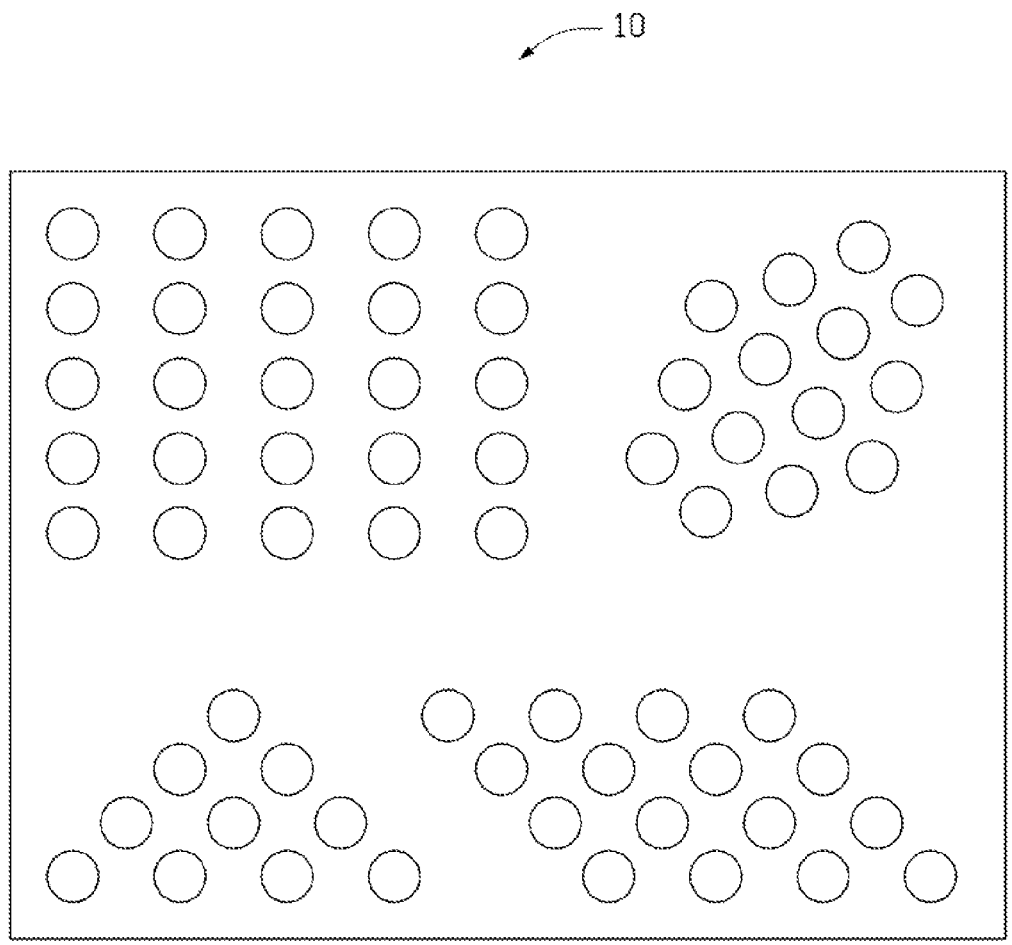
FIG. 4 is a view of one embodiment of a three-dimensional nano-structure array forming a pattern group.

The three-dimensional nano-structures 102 can be arranged in the form of an array. The three-dimensional nano-structures 102 in the array can be hexagonally arranged, squarely arranged, or concentrically arranged. The three-dimensional nano-structures 102 can be arranged to form a single pattern or multiple pattern groups. The single pattern can be a triangle, parallelogram, diamond, square, trapezoid, rectangle, or circle. In one embodiment, a multiple pattern group includes four different single patterns as shown in FIG. 4.

The metal layer 101 is a continuous structure and covers the entire surface of the substrate 100 and the surfaces of the three-dimensional nano-structures 102. The metal layer 101 can be a single-layer or a multi-layer structure. The thickness of the metal layer 101 can be in a range from about 2 nanometers to about 200 nanometers. The material of the metal layer 101 can be gold, silver, copper, iron, nickel, aluminum, or any alloy thereof. The metal layer 101 can be uniformly deposited on the surface of the substrate 100 by a method of electron beam evaporation, chemical vapor deposition (CVD), or sputtering. In one embodiment, the metal layer 101 is a silver layer with a thickness of about 20 nanometers. At the gap between two adjacent three-dimensional nano-structures 102, a surface plasmon resonance (SPR) is produced on a surface of the metal layer 101 so that the surface-enhanced Raman scattering (SERS) of the carrier 10 will be enhanced. The enhancement factor of SERS of the carrier 10 can be in a range from about $10^5$ to about $10^{15}$. In one embodiment, the enhancement factor of SERS of the carrier 10 is about $10^{10}$.

Figure 5:
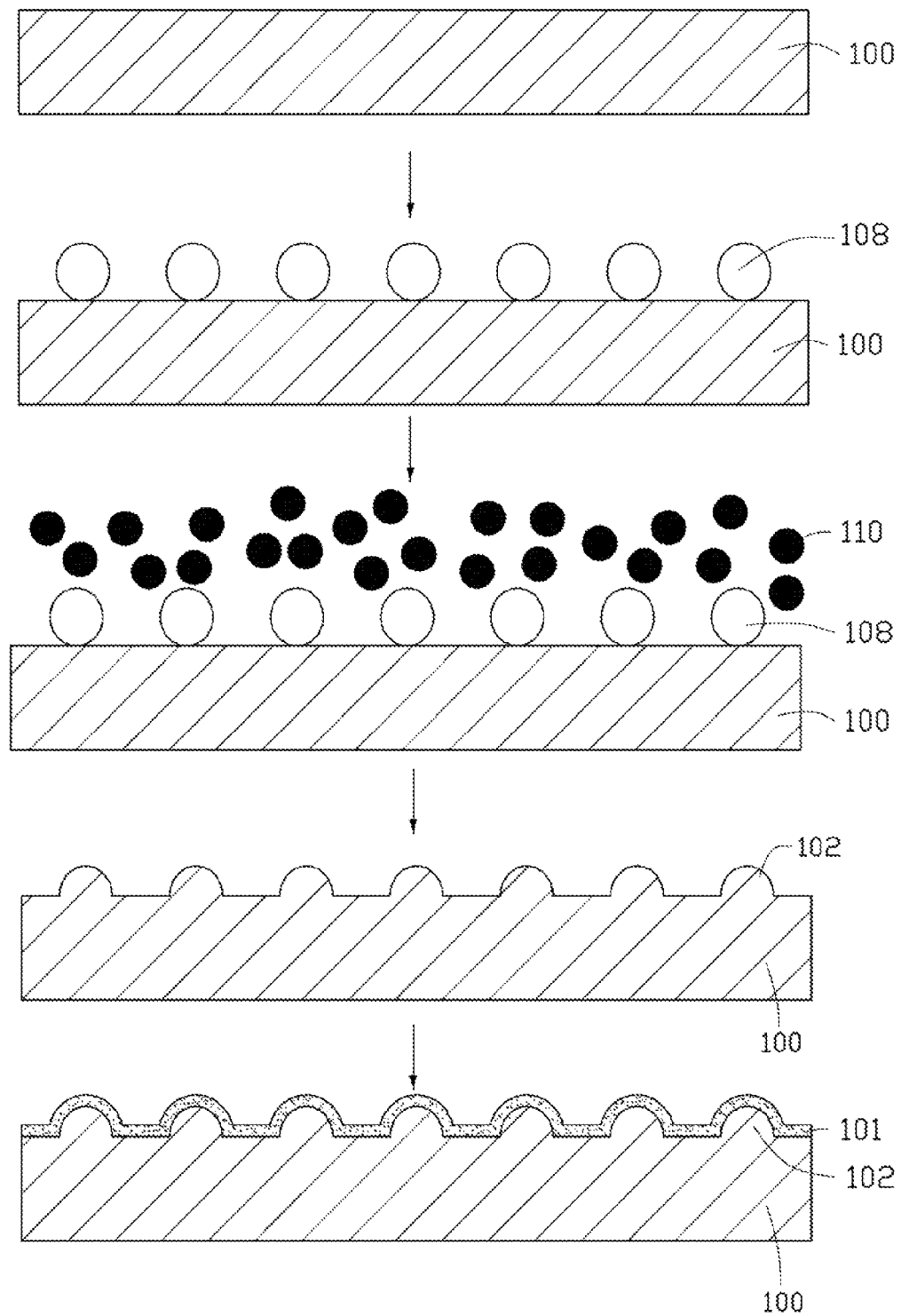
FIG. 5 shows a process of one embodiment of a method for making a carrier for single molecule detection.

Referring to FIG. 5, a method for making a carrier 10 for single molecule detection of one embodiment includes the following steps of:

step (a), providing a substrate 100;

step (b), forming a monolayer nanosphere array 108 on a surface of the substrate 100;

step (c), etching the substrate 100 by the monolayer nanosphere array 108 in a reactive atmosphere 110 to form a number of three-dimensional nano-structures 102;

step (d), removing the monolayer nanosphere array 108; and step (e), depositing a metal layer 101 on the surface of the substrate 100 to cover the three-dimensional nano-structures 102.

In step (a), the substrate 100 can be made of a material such as glass, quartz, silicon (Si), silicon dioxide ($SiO_2$), silicon nitride ($Si_3N_4$), gallium nitride (GaN), gallium arsenide (GaAs), alumina ($Al_2O_3$), or magnesia (MgO). In one embodiment, the substrate 100 is a silicon dioxide layer with a thickness from about 200 micrometers to about 300 micrometers.

An optional step (f) of hydrophilic treating the substrate 100 can be performed after step (a) and before step (b). The step (f) can include the following substeps of:

step (f1): cleaning the substrate 100;

step (f2): soaking the substrate 100 in a hydrophilic treatment solution; and step (f3): rinsing and drying the substrate 100.

In step (f1), the cleaning process can be any standard cleaning process such as a process used in cleanroom.

In step (f2), the hydrophilic treatment solution can be a mixture of $NH_3$, $H_2O$, $H_2O_2$, and $H_2O$ at a temperature in a range from about 30° C. to about 100° C. The soaking time is in a range from about 30 minutes to about 60 minutes. The hydrophilic treatment solution can be a mixture of $NH_3 \cdot H_2O$: $H_2O_2$:$H_2O$ at about 0.5-1:1:5. In one embodiment, the hydrophilic treatment solution is $NH_3 \cdot H_2O$:$H_2O_2$:$H_2O$ at about 0.6:1:5 with a temperature in a range from about 70° C. to about 80° C., and the soaking time of about 40 minutes.

In step (f3), the substrate 100 can be rinsed in deionized water for about 2 times to about 3 times. The substrate 100 can be dried by nitrogen gas blowing.

Furthermore, an optional step (g) of a secondary hydrophilic treatment can be performed after step (f) and before step (b). In step (g), the substrate 100 is soaked in about 1 wt. % to about 5 wt. % of SDS solution for about 2 hours to about 24 hours to obtain a hydrophilic surface. In one embodiment, the substrate 100 is soaked in about 2 wt. % of SDS solution for about 10 hours.

Step (b) can include the substeps of:

step (b1), preparing a nanosphere solution;

step (b2), forming a monolayer nanosphere solution on the substrate 100; and step (b3), drying the monolayer nanosphere solution.

In step (b1), the diameter of the nanosphere can be in range from about 60 nanometers to about 500 nanometers, such as about 100 nanometers, about 200 nanometers, about 300 nanometers, or about 400 nanometers. The material of the nanosphere can be polymer or silicon. The polymer can be polymethyl methacrylate (PMMA) or polystyrene (PS). In one embodiment, a PS nanosphere solution can be synthesized by emulsion polymerization.

In step (b2), the monolayer nanosphere solution can be formed on the substrate 100 by dipping.

The method of dipping can include the substeps of:

step (b21), diluting the nanosphere solution;

step (b22), inserting the substrate 100 into the diluted nanosphere solution; and step (b23), drawing the substrate 100 out of the diluted nanosphere solution.

In step (b21), the nanosphere solution can be diluted by water or ethanol. In one embodiment, about 3 microliters to about 5 microliters PS nanosphere solution of about 0.01 wt. % to about 10 wt. % is mixed with about 150 milliliters water, and about 1 microliter to about 5 microliters dodecylsodiumsulfate (SDS) of about 2 wt. % to obtain a mixture. The mixture can be kept for about 30 minutes to about 60 minutes. In addition, about 1 microliter to about 3 microliters SDS of about 4 wt % can be added in the mixture to adjust the surface tension of the PS nanospheres.

In step (b22) and step (b23), the substrate 100 is inserted into and drawn out of the diluted nanosphere solution slowly and obliquely. An angle between the surface of the substrate 100 and the level can be in a range from about 5 degrees to about 15 degrees. The speed of inserting and drawing the substrate can be in a range from about 3 millimeters per hour to about 10 millimeters per hour. In one embodiment, the angle between the surface of the substrate 100 and the level is about 9 degrees, and the velocity of inserting and drawing the substrate is about 5 millimeters per hour.

In step (b2), the monolayer nanosphere solution can be formed on the substrate 100 by spin coating. The method of spin-coating includes the substeps of:

step (b21a), diluting the nanosphere solution;

step (b22a), dripping some diluted nanosphere solution on the surface of the substrate 100;

step (b23a), spinning the substrate 100 at a speed from about 400 revolutions per minute to about 500 revolutions per minute for about 5 seconds to about 30 seconds;

step (b24a), increasing the spinning speed of the substrate 100 to a range from about 800 revolutions per minute to about 1000 revolutions per minute and maintaining it for about 30 seconds to about 2 minutes;

step (b25a): increasing the spinning speed of the substrate 100 to a range from about 1400 revolutions per minute to about 1500 revolutions per minute and maintaining it for about 10 seconds to about 20 seconds.

In step (b21a), about 10 wt % of the PS nanosphere solution can be diluted by mixing with a diluting agent at a volume ratio of about 1:1. The diluting agent can be a mixture of SDS and ethanol with a volume ratio of about 1:4000.

In step (b22a), the nanosphere solution of about 3 microliters to about 4 microliters is entirely dispersed onto the surface of the substrate 100.

In steps (b23a) to step (b25a), a close-packed monolayer nanosphere solution is generated from the center to the edge of the substrate 100.

Figure 6:
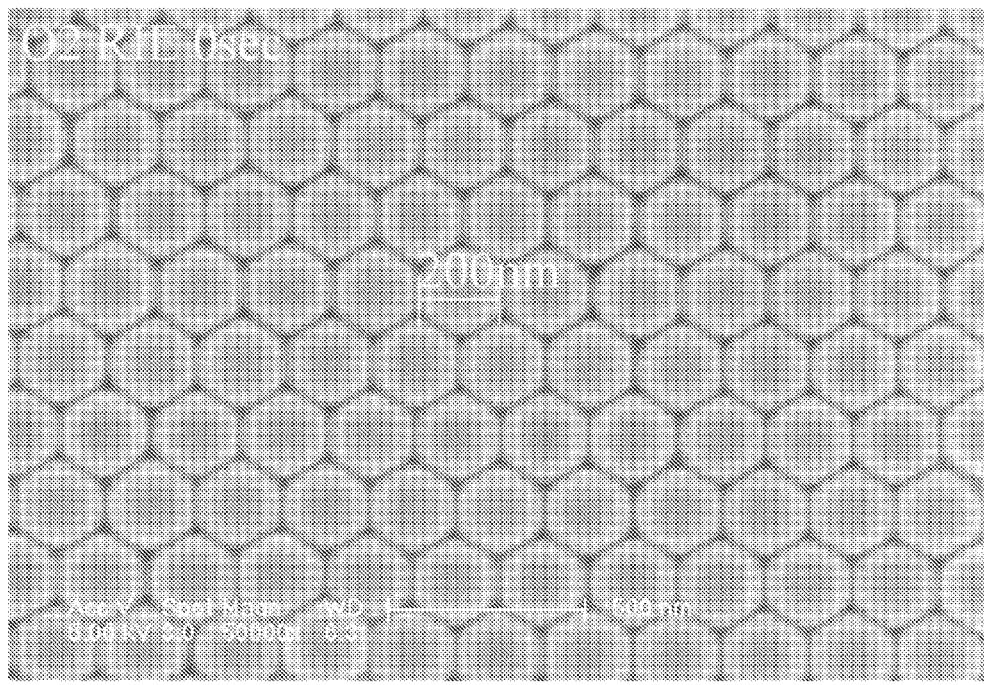
FIG. 6 is an SEM image of a hexagonally close-packed monolayer nanosphere array of one embodiment of a method for making a carrier for single molecule detection.

In step (b3), the monolayer nanosphere array 108 can be obtained. The monolayer nanosphere array 108 includes a number of monolayer nanospheres hexagonally close-packed, squarely close-packed, or concentrically close-packed. As shown in FIG. 6, in one embodiment, the monolayer nanospheres are hexagonally close-packed.

An optional step (b4) of baking the monolayer nanosphere array 108 can be performed after step (b3). The baking temperature can range from about 50° C. to about 100° C. and the baking time can range from about 1 minute to about 5 minutes.

In step (c), the monolayer nanosphere array 108 can be used as a mask. In one embodiment, step (c) can be carried out in a microwave plasma system at a Reaction-Ion-Etching mode. The microwave plasma system produces the reactive atmosphere 110. The reactive atmosphere 110 with lower ions energy reaches a surface of the monolayer nanosphere array 108. The reactive atmosphere 110 can etch the substrate 100 by using the monolayer nanosphere array 108 as a mask. Thus, the three-dimensional nano-structures 102 are obtained.

In one embodiment, the reactive atmosphere 110 consists of chlorine gas ($Cl_2$), argon gas (Ar), and oxygen gas ($O_2$). The input flow rate of the chlorine gas can be in a range from about 10 scc/m to about 60 scc/m. The input flow rate of the argon gas can be in a range from about 4 scc/m to about 20 scc/m. The input flow rate of the oxygen gas can be in a range from about 4 scc/m to about 20 scc/m. The power of the plasma system can be in a range from about 40 Watts to about 70 Watts. The working gas pressure of the reactive atmosphere 110 can be in a range from about 2 Pa to about 10 Pa. The tailoring and etching time in the reactive atmosphere 110 can be in a range from about 1 minute to about 2.5 minutes. The ratio between the power of the plasma system and the working gas pressure of the reactive atmosphere 110 can be less than 20:1. In one embodiment, the ratio between the power of the plasma system and the working gas pressure of the reactive atmosphere 110 can be less than 10:1.

Furthermore, an adjusting gas can be added into the reactive atmosphere 110 to adjust the tailoring and etching time. The adjusting gas can be boron trichloride ($BCl_3$), carbon tetrafluoride ($CF_4$), sulfur hexafluoride ($SF_6$), trifluoromethane ($CHF_3$), or a combination thereof. The input flow rate of the adjusting gas can be in a range from about 20 scc/m to about 40 scc/m.

The shape of the three-dimensional nano-structures 102 can be determined by the etching condition such as the reactive atmosphere 110, etching time, working gas pressure and so on. For example, the shape of the three-dimensional nano-structures 102 can be hemispherical, semi-ellipsoidal, or cylindrical.

In step (d), the monolayer nanosphere array 108 can be removed by dissolving in a stripping agent such as tetrahydrofuran (THF), acetone, butanone, cyclohexane, hexane, methanol, or ethanol. The monolayer nanosphere array 108 can also be removed by peeling with an adhesive tape.

In step (e), the metal layer 101 can be deposited on the surface of the substrate 100 by a method of electron beam evaporation, chemical vapor deposition (CVD), or sputtering. The thickness of the metal layer 101 can be in a range from about 2 nanometers to about 200 nanometers. The material of the metal layer 101 can be gold, silver, copper, iron, nickel, aluminum or alloy thereof.

Figure 7:
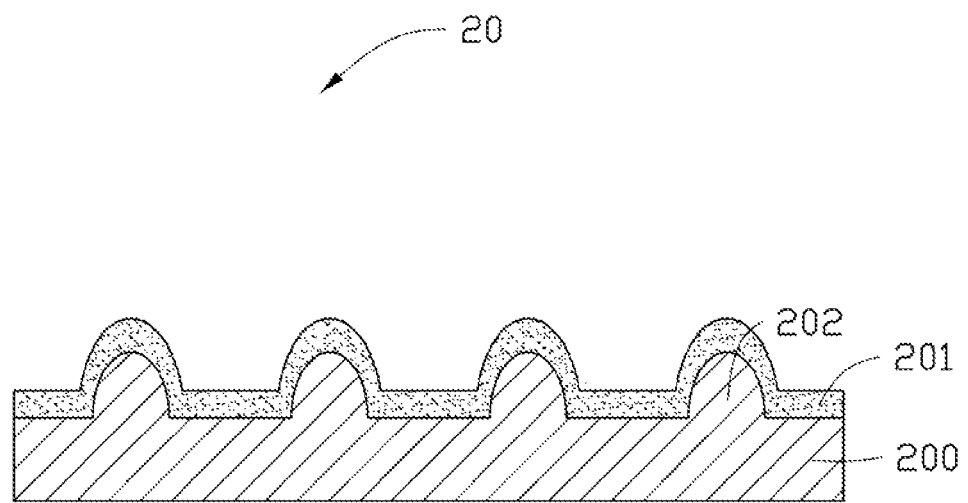
FIG. 7 is a cross-sectional view, of one embodiment of a carrier for single molecule detection.
Figure 8:
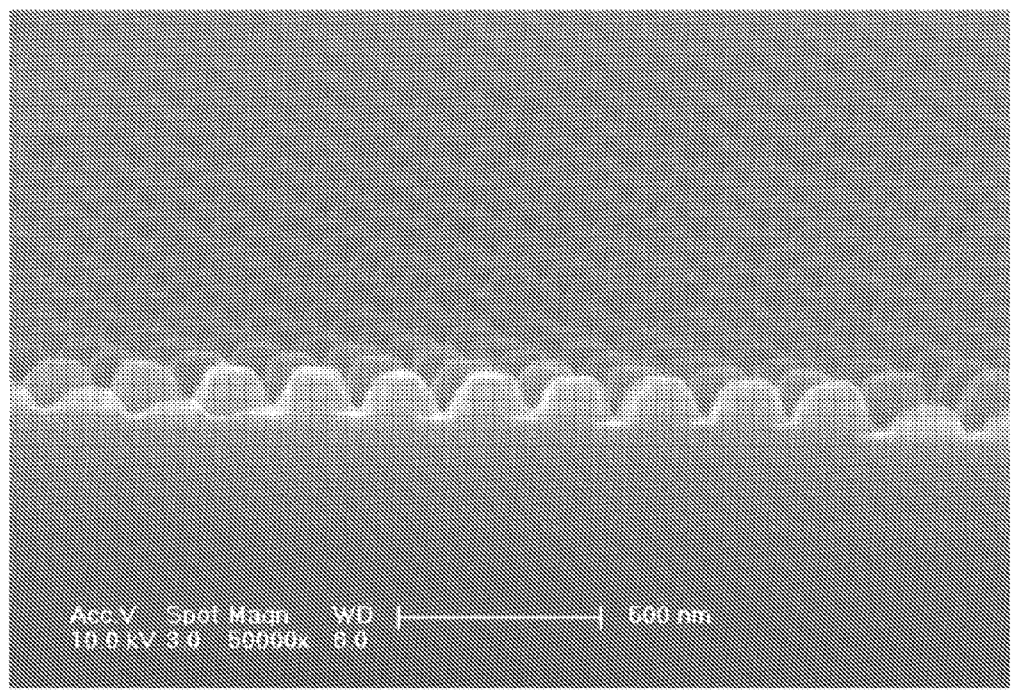
FIG. 8 is an SEM image of a carrier for single molecule detection of FIG. 7.

Referring to FIGS. 7 to 8, a carrier 20 for single molecule detection of one embodiment includes a substrate 200 and a metal layer 201. The substrate 200 has a surface and includes a number of three-dimensional nano-structures 202 protruding from the surface. The metal layer 201 is located on the surface of the substrate 200 and covers the three-dimensional nano-structures 202. The carrier 20 is similar to the carrier 10 described above except that each of the three-dimensional nano-structures 202 is a semi-ellipsoidal bulge protruding out from the surface of the substrate 200.

The semi-ellipsoidal bulge has a round bottom surface having a diameter in a range from about 50 nanometers to about 1000 nanometers. The height of the semi-ellipsoidal bulge can be in a range from about 50 nanometers to about 1000 nanometers. The two adjacent semi-ellipsoidal bulges are substantially equidistantly arranged. The distance between the bottom surfaces of two adjacent semi-ellipsoidal bulges can be in a range from about 0 nanometers to about 50 nanometers. In one embodiment, the diameter of the bottom surface of the semi-ellipsoidal bulge is in a range from about 50 nanometers to about 200 nanometers, the height of the semi-ellipsoidal bulge is in a range from about 100 nanometers to about 500 nanometers, and the distance between the bottom surfaces of two adjacent semi-ellipsoidal bulges is about 40 nanometers.

The metal layer 201 is a continuous structure and covers the entire surface of the substrate 200. The enhancement factor of SERS of the carrier 20 can be in a range from about $10^5$ to about $10^{15}$. In one embodiment, the enhancement factor of SERS of the carrier 20 is about $10^6$.

Figure 9:
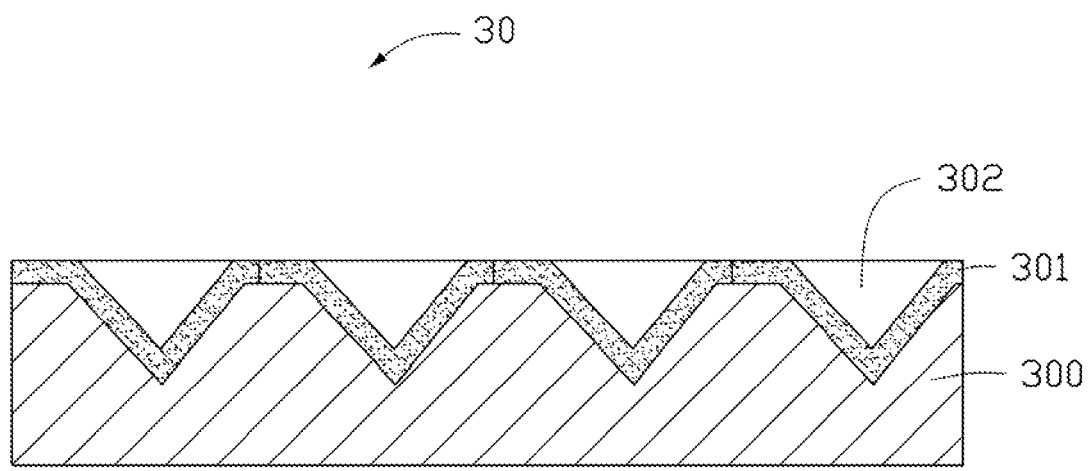
FIG. 9 is a cross-sectional view, of one embodiment of a carrier for single molecule detection.
Figure 10:
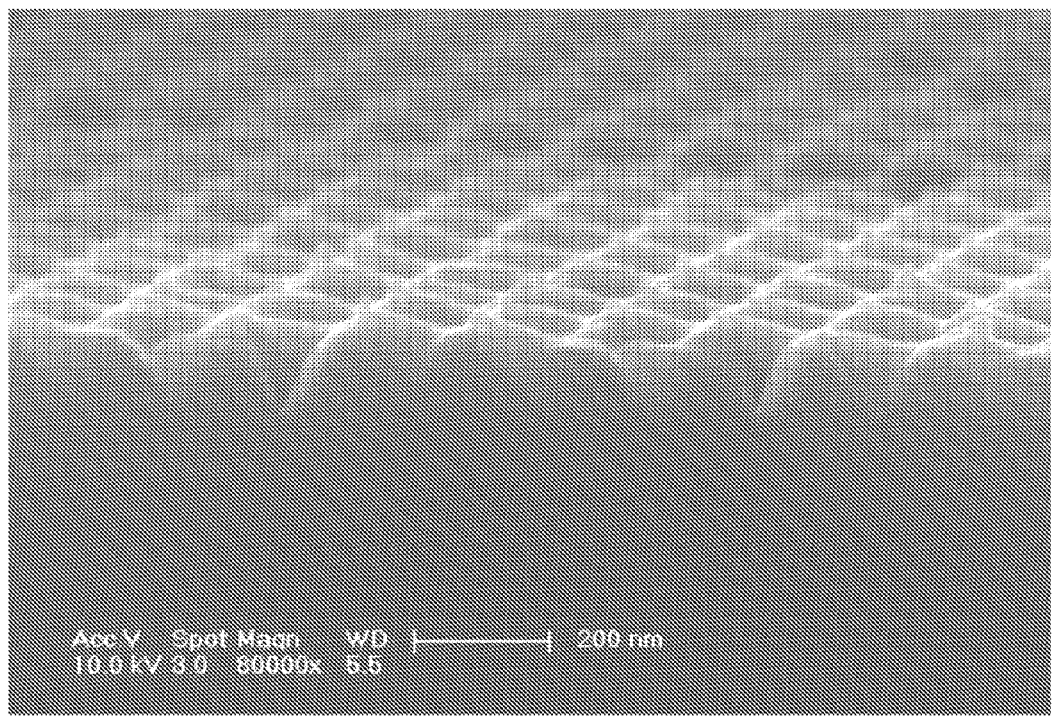
FIG. 10 is an SEM image of a carrier for single molecule detection of FIG. 9.

Referring to FIGS. 9 to 10, one embodiment of a carrier 30 for single molecule detection includes a substrate 300 and a metal layer 301. The substrate 300 has a surface and defines a number of three-dimensional nano-structures 302 at the surface. The metal layer 301 is located on the surface of the substrate 300 and covers the three-dimensional nano-structures 302. The carrier 30 is similar to the carrier 10 described above except that each of the three-dimensional nano-structures 302 is an pyramid shaped depression in the substrate 300 from the surface thereof.

The shape of the bottom surface of the depression can be triangular, rectangular, or square. The depth of the depression can be in a range from about 50 nanometers to about 1000 nanometers. The vertex angle $\alpha$ of the depression can be in a range from about 15 degrees to about 70 degrees. In one embodiment, the shape of the bottom surface of the depression is an equilateral triangle with a side length in a range from about 50 nanometers to about 200 nanometers. The depth of the depression can be in a range from about 100 nanometers to about 500 nanometers. The vertex angle $\alpha$ of the depression can be about 30 degrees. The depressions can be substantially equidistantly arranged. The distance between the bottom surfaces of two adjacent depression can be in a range from about 0 nanometers to about 50 nanometers.

The metal layer 301 is a continuous structure and covers the entire surface of the substrate 300 and the inner surfaces of the three-dimensional nano-structures 302. The enhancement factor of SERS of the carrier 20 can be in a range from about $10^5$ to about $10^{15}$. In one embodiment, the enhancement factor of SERS of the carrier 30 is about $10^8$.

Figure 11:
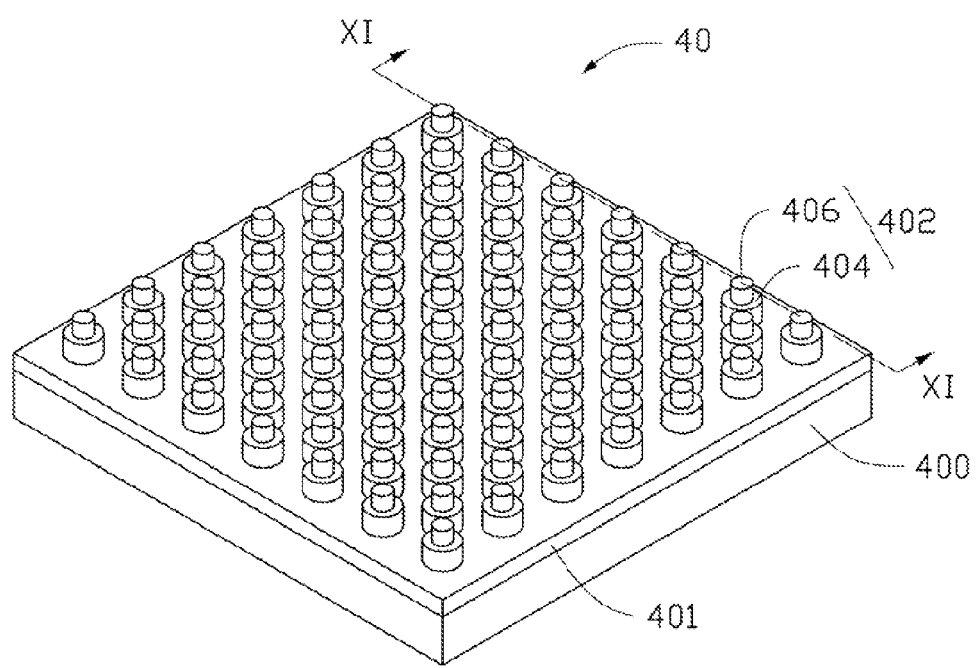
FIG. 11 is an isometric view of one embodiment of a carrier for single molecule detection.
Figure 12:
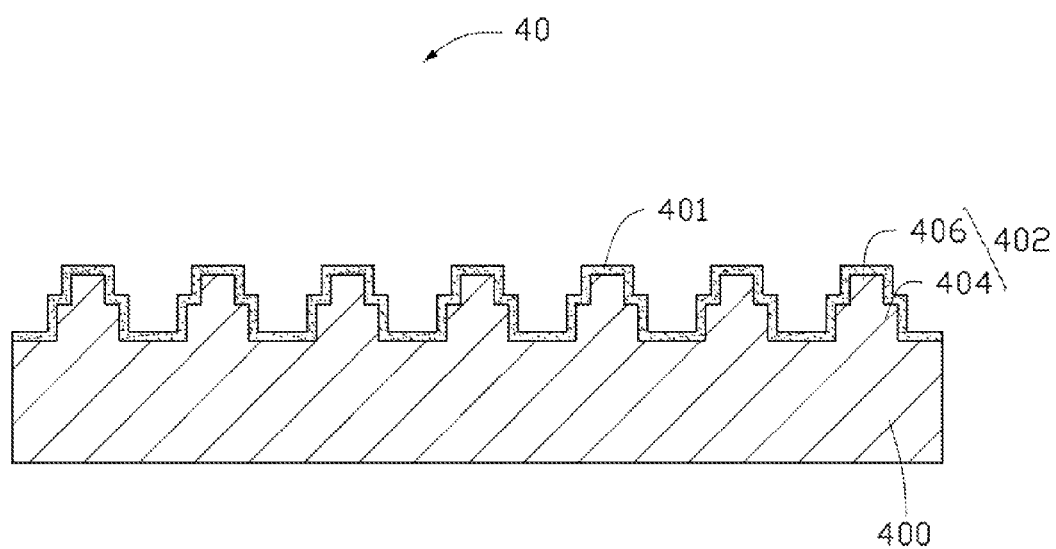
FIG. 12 is a cross-sectional view, along a line XII-XII of FIG. 11.
Figure 13:
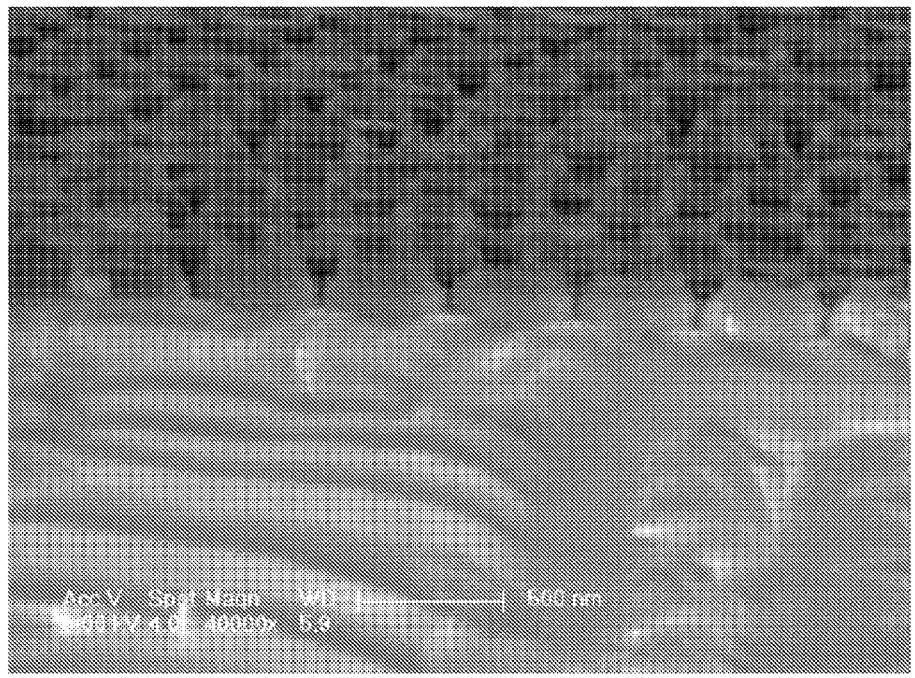
FIG. 13 is an SEM image of a carrier for single molecule detection of FIG. 11.

Referring to FIGS. 11 to 13, one embodiment of a carrier 40 for single molecule detection includes a substrate 400 and a metal layer 401. The substrate 400 has a surface and includes a number of three-dimensional nano-structures 402 protruding from the surface. The metal layer 401 is located on the surface of the substrate 400 and covers the three-dimensional nano-structures 402. The carrier 40 is similar to the carrier 10 described above except that each of the three-dimensional nano-structures 402 is a stepped bulge protruding upwardly from the surface of the substrate 400.

The stepped bulge can be a multi-layer structure such as a multi-layer frustum of a prism, a multi-layer frustum of a cone, or a multi-layer cylinder. In one embodiment, the three-dimensional nano-structure 402 is a stepped cylindrical structure. The size of the three-dimensional nano-structure 402 is less than or equal to 1000 nanometers, namely, the length, the width, and the height are less than or equal to 1000 nanometers. In one embodiment, the length, the width, and the height of the three-dimensional nano-structure 402 are in a range from about 10 nanometers to about 500 nanometers.

In one embodiment, the three-dimensional nano-structure 402 is a two-layer cylindrical structure including a first cylinder 404 and a second cylinder 406 extending from a top of the first cylinder 404. The diameter of the second cylinder 406 is less than the diameter of first cylinder 404 to form the stepped structure. The first cylinder 404 is located on the surface of the substrate 400. The first cylinder 404 extends substantially perpendicularly and upwardly from the surface of the substrate 400. The second cylinder 406 extends substantially perpendicularly and upwardly from a top surface of the first cylinder 404. The second cylinder 406 and the first cylinder 404 can be coaxial. The second cylinder 406 and the first cylinder 404 can be an integral structure, namely the second cylinder 406 is a protruding body of the first cylinder 404. The two adjacent three-dimensional nano-structures 402 are substantially equidistantly arranged.

In one embodiment, the diameter of the first cylinder 404 can be in a range from about 30 nanometers to about 1000 nanometers. The height of the first cylinder 404 can be in a range from about 50 nanometers to about 1000 nanometers. The diameter of the second cylinder 406 can be in a range from about 10 nanometers to about 500 nanometers. The height of the second cylinder 406 can be in a range from about 20 nanometers to about 500 nanometers. The distance between two adjacent first cylinders 404 can be in a range from about 10 nanometers to about 1000 nanometers.

In one embodiment, the diameter of the first cylinder 404 can be in a range from about 50 nanometers to about 200 nanometers. The height of the first cylinder 404 can be in a range from about 400 nanometers to about 500 nanometers. The diameter of the second cylinder 406 can be in a range from about 20 nanometers to about 200 nanometers. The height of the second cylinder 406 can be in a range from about 100 nanometers to about 300 nanometers. The distance between the two adjacent first cylinders 404 can be in a range from about 10 nanometers to about 30 nanometers.

In one embodiment, the diameter of the first cylinder 404 is about 380 nanometers, the height of the first cylinder 404 is about 105 nanometers, the diameter of the second cylinder 406 is about 280 nanometers, the height of the second cylinder 406 is about 55 nanometers, and the distance between two adjacent first cylinders 404 is about 30 nanometers.

Furthermore, each of the three-dimensional nano-structures 402 can be a three-layer cylindrical structure. The SERS of the carrier 40 will be further enhanced because the SPR can be produced both in the first gap between two adjacent first cylinders 404 and in the second gap between two adjacent second cylinders 406.

One embodiment of a method for making a carrier 40 for single molecule detection includes the following steps of:

step (H1), providing a substrate 400;

step (H2), forming a monolayer nanosphere array 108 on a surface of the substrate 400;

step (H3), simultaneously tailoring the monolayer nanosphere array 108 and etching the substrate 400 by the monolayer nanosphere array 108 in a reactive atmosphere 110 to form a number of stepped bulges;

step (H4), removing the monolayer nanosphere array 108; and step (H5), depositing a metal layer 401 on the surface of the substrate 400 to cover the three-dimensional nano-structures 402.

The method for making the carrier 40 is similar to the method for making the carrier 10 described above except that in step (H3), simultaneously tailoring the monolayer nanosphere array 108 during etching the substrate 400.

In step (H3), the reactive atmosphere 110 can tailor the monolayer nanosphere array 108 and simultaneously etch the substrate 400 by using the monolayer nanosphere array 108 as a mask. The nanospheres become smaller and the gap between the adjacent nanospheres becomes greater during the process. As the gap between the adjacent nanospheres increases, more portions of the substrate 400 can be etched. Thus, the three-dimensional nano-structures 402 with the stepped structure are obtained.

Figure 14:
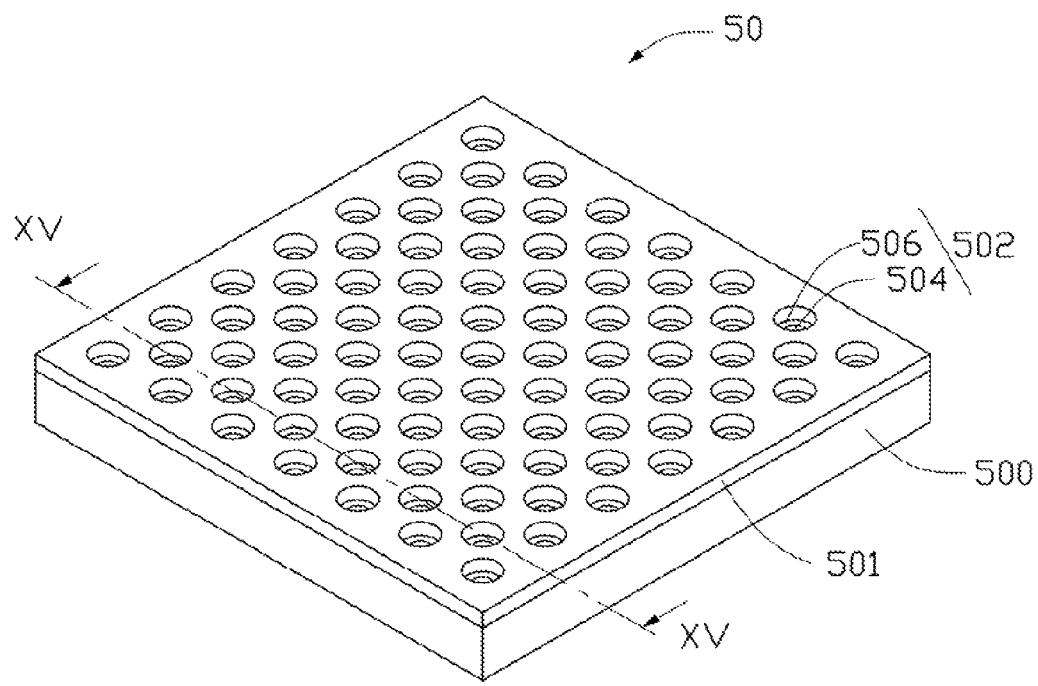
FIG. 14 is an isometric view of one embodiment of a carrier for single molecule detection.
Figure 15:
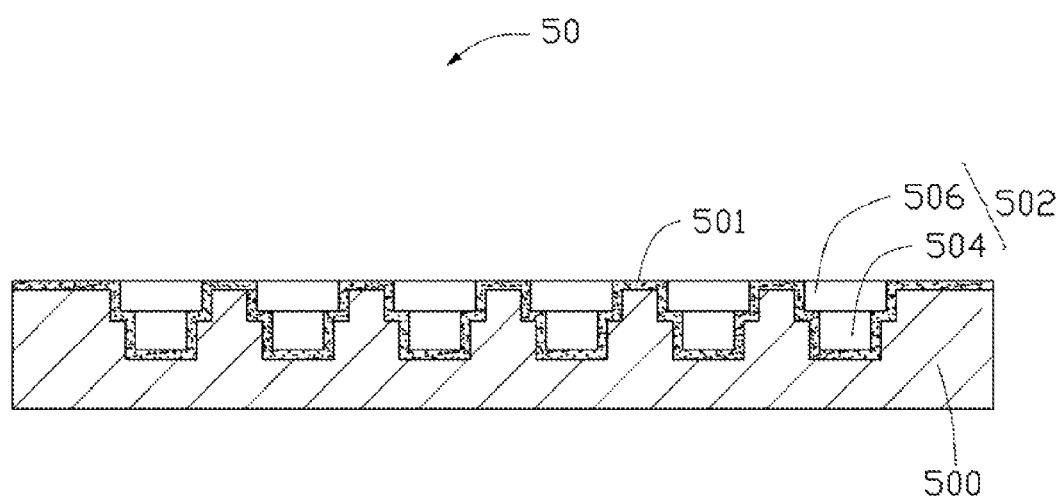
FIG. 15 is a cross-sectional view, along a line XV-XV of FIG. 14.

Referring to FIGS. 14 to 15, one embodiment of a carrier 50 for single molecule detection includes a substrate 500 and a metal layer 501. The substrate 500 has a surface and defines a number of three-dimensional nano-structures 502 at the surface. The metal layer 501 is located on the surface of the substrate 500 and covers the three-dimensional nano-structures 502. The carrier 50 is similar to the carrier 40 described above except that each of the three-dimensional nano-structures 502 is a stepped depression in the substrate 500 from the surface thereof and includes two communicating spaces.

A stepped configuration is formed where the two communicating spaces join. The shape of the three-dimensional nano-structure 502 can be a multi-layer structure such as a multi-layer frustum of a prism, a multi-layer frustum of a cone, or a multi-layer cylinder. In one embodiment, the shape of the three-dimensional nano-structure 502 is a two-layer cylindrical structure including a first cylindrical space 504 and a second cylindrical space 506 substantially coaxially aligned with the first cylindrical space 504. The second cylindrical space 506 is adjacent to the surface of the substrate 500. The diameter of the second cylindrical space 506 is greater than the diameter of first cylindrical space 504.

The metal layer 501 is located on the surface of the substrate 500 and the inner surfaces of the three-dimensional nano-structures 502. The SERS of the carrier 50 will be further enhanced because the SPR can be produced both in the first cylindrical space 504 and the second cylindrical space 506.

One embodiment of a method for making a carrier 50 for single molecule detection of one embodiment includes the following steps of:

step (K1), providing a substrate 500;

step (K2), forming a mask defining a number of holes at a surface of the substrate 500;

step (K3), simultaneously tailoring the mask and etching the substrate 500 by the mask in a reactive atmosphere 110 to form a number of stepped depressions;

step (K4), removing the mask; and step (K5), depositing a metal layer 501 on the surface of the substrate 500 to cover the stepped depressions.

The method for making the carrier 50 is similar to the method for making the carrier 40 described above except that in step (K2), the mask is a continuous film defining a number of holes arranged in the form of array. The mask can be made of polymer such as poly ethylene terephthalate (PET), polycarbonate (PC), polyethylene (PE), or polyimide (PI). The mask can be formed by nano-imprint or template deposition.

In step (K3), because the reactive atmosphere can tailor the mask and simultaneously etch the substrate 500 by the mask, the holes become greater and the gap between the adjacent holes becomes smaller during the process. As the holes become larger, more of the substrate 500 can be etched. Thus, the three-dimensional nano-structures 502 with a stepped depression are obtained.

Furthermore, one embodiment of a method for using the carriers described above to detect single molecule includes the following steps of:

step (M1), providing a carrier including a substrate and a metal layer, wherein the substrate has a surface and comprises a number of three-dimensional nano-structures at the surface, the metal layer is located on the surface of the substrate and covers the three-dimensional nano-structures;

step (M2), disposing single molecule samples on a surface of the metal layer; and step (M3), detecting the single molecule samples with a detector.

In step (M1), the carrier can be carrier 10, 20, 30, 40, 50 described above.

In step (M2), disposing single molecule samples includes the following substeps of:

step (M21): providing a single molecule sample solution;

step (M22): immersing the carrier into the single molecule sample solution; and step (M23): drawing the carrier out of the single molecule sample solution.

In step (M21), the molecular concentration of the single molecule sample solution can be in a range from about $10^{-7}$ mmol/L to about $10^{-12}$ mmol/L. In one embodiment, the molecular concentration of the single molecule sample solution is about $10^{-10}$ mmol/L.

In step (M22), the carrier is kept in the single molecule sample solution for a time from about 2 minutes to about 60 minutes so that the single molecule samples can be dispersed on the metal layer uniformly. In one embodiment, the carrier is kept in the single molecule sample solution for about 10 minutes.

In step (M22), the carrier is rinsed in water or ethanol for about 5 times to about 15 times and dried.

In step (M3), a Raman Spectroscopy system is used to detect the single molecule samples. In one embodiment, the Raman Spectroscopy system has an excitation source of He—Ne, an excitation wavelength of 633 nanometers, an excitation time of 10 seconds, a device power of 9.0 mW, and a working power of 9.0 mW×0.05×1.

Figure 16:
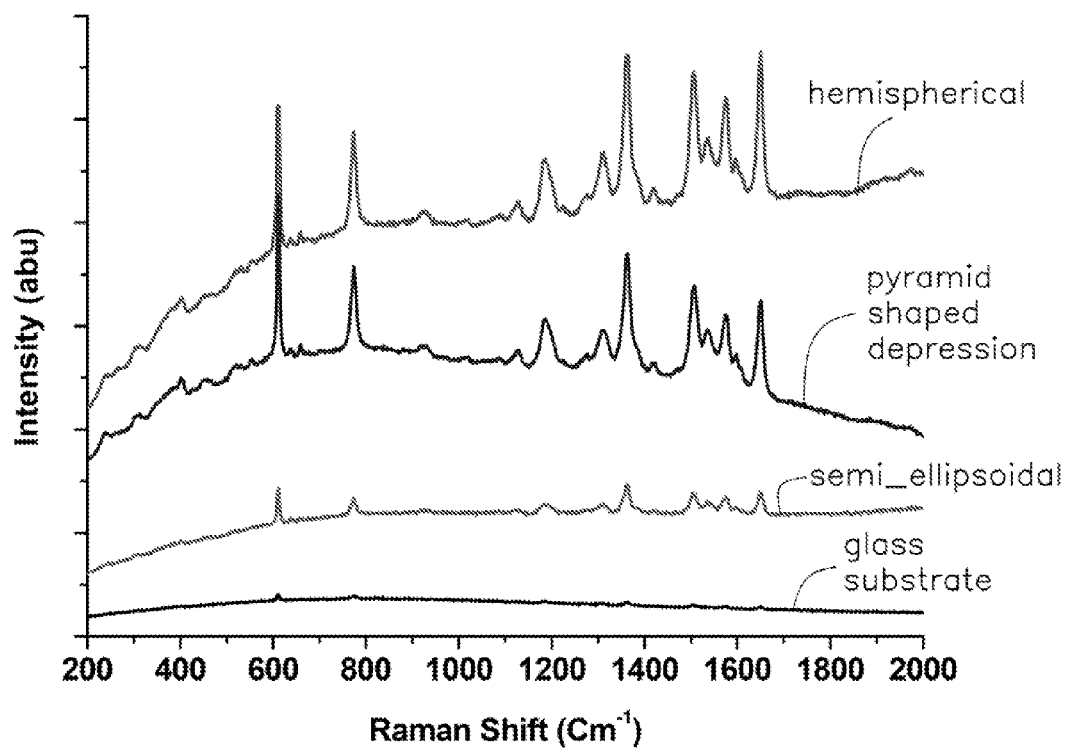
FIG. 16 shows a Raman spectroscopy of Rhodamine molecules using different carriers for detection.

Rhodamine molecule samples are disposed on the carrier 10, 20, 30, and a glass substrate respectively, and detected by the Raman Spectroscopy system. FIG. 16 shows a Raman spectroscopy of Rhodamine molecules using different carriers for detection. The intensities of the Raman spectroscopy of the samples disposed on the carrier 10 with hemispherical bulge and the samples disposed on the carrier 30 with pyramid shaped depressions are strong.

Compare to the aggregated silver particle film, the carrier has the following advantages. First, if the aggregated silver particle film is large area, the uniformity of the aggregated silver particle film is relatively low. However, the uniformity of the carrier in large area is high, so the reproducibility of the Raman scattering signal is high. Second, the size of the three-dimensional nano-structures is smaller than the aggregated silver particles, so the density of the hot-spots of the carrier is high. Thus, the sensitivity of the Raman scattering is high. Third, the geometry, size and gap of the aggregated silver particle are uncontrollable. However, the geometry, size and gap of the three-dimensional nano-structures of the carrier can be controlled by the etching condition such as the reactive atmosphere, etching time, working gas pressure.

It is to be understood that the above-described embodiments are intended to illustrate rather than limit the disclosure. Any elements described in accordance with any embodiments is understood that they can be used in addition or substituted in other embodiments. Embodiments can also be used together. Variations may be made to the embodiments without departing from the spirit of the disclosure. The above-described embodiments illustrate the scope of the disclosure but do not restrict the scope of the disclosure.

Depending on the embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

What is claimed is:

1. A method for detecting single molecule, the method comprising:

making a carrier comprising a substrate and a metal layer, the substrate having a surface and comprising a plurality of three-dimensional nano-structures on the surface, the metal layer is configured to cover the surface of the substrate and the three-dimensional nano-structures, wherein the carrier is fabricated by the steps of:

making the substrate;

forming a mask on the substrate, the mask comprising a polymer monolayer nanosphere array;

simultaneously etching the substrate using the mask and tailoring the mask to form an integral structure comprising a base having a surface and the plurality of three-dimensional nano-structures on the surface of the base, wherein each of the plurality of three-dimensional nano-structures is a stepped cylindrical bulge protruding from the surface of the base and comprises a first cylinder on the base and a second cylinder on the first cylinder, a diameter of the first cylinder is greater than a diameter of the second cylinder, the simultaneously etching the substrate using the mask and tailoring the mask is performed in a reactive atmosphere consisting of chlorine, argon gas, and oxygen gas, the etching the substrate comprises chemical etching the substrate with chlorine gas, and the tailoring the mask comprises chemical etching the polymer monolayer nanosphere array with oxygen gas;

removing the mask; and depositing the metal layer on the substrate;

disposing single molecule samples on the metal layer; and detecting the single molecule samples using a detector.

2. The method of claim 1, wherein the polymer monolayer nanosphere array is formed by the steps of:

preparing a nanosphere solution;

forming a monolayer nanosphere solution on the substrate; and drying the monolayer nanosphere solution.

3. The method of claim 1, wherein the metal layer is deposited on the substrate by electron beam evaporation, chemical vapor deposition, or sputtering.

4. The method of claim 1, wherein a distance between adjacent two of the plurality of three-dimensional nano-structures is in a range from about 0 nanometers to about 50 nanometers.

5. The method of claim 1, wherein an enhancement factor of SERS of the carrier is in a range from about 105 to about 1015.

6. The method of claim 1, wherein the step of disposing the single molecule samples comprises steps of:

providing a single molecule sample solution;

immersing the carrier into the single molecule sample solution; and drawing the carrier out of the single molecule sample solution.

7. The method of claim 6, wherein a molecular concentration of the single molecule sample solution is in a range from about $10^{-7}$ mmol/L to about $10^{-12}$ mmol/L.

8. The method of claim 1, wherein the detector is a Raman Spectroscopy system.

9. The method of claim 1, wherein the simultaneously etching the substrate using the mask and tailoring the mask is performed by a plasma system.

10. The method of claim 9, wherein an input flow rate of the chlorine gas is in a range from about 10 scc/m to about 60 scc/m, an input flow rate of the argon gas is in a range from about 4 scc/m to about 20 scc/m, and an input flow rate of the oxygen gas is in a range from about 4 scc/m to about 20 scc/m.

11. The method of claim 10, wherein a power of the plasma system is in a range from about 40 Watts to about 70 Watts.

12. The method of claim 11, wherein a working gas pressure of the reactive atmosphere is in a range from about 2 Pa to about 10 Pa.

13. The method of claim 12, wherein a time of the tailoring of the mask and the etching of the substrate in the reactive atmosphere is in a range from about 1 minute to about 2.5 minutes.

14. The method of claim 13, wherein a ratio between the power of the plasma system and the working gas pressure of the reactive atmosphere is less than 20:1, unit of the power is Watt, and unit of the working gas pressure is Pa.

15. The method of claim 14, wherein the ratio between the power of the plasma system and the working gas pressure of the reactive atmosphere is less than 10:1, unit of the power is Watt, and unit of the working gas pressure is Pa.

16. A method for detecting single molecules, the method comprising:

making a carrier comprising a substrate and a metal layer, wherein the substrate has a surface and comprises a plurality of stepped three-dimensional nano-structures on the surface, the metal layer is configured to cover the surface of the substrate and the plurality of stepped three-dimensional nano-structures, wherein the carrier is fabricated by the steps of:

making the substrate;

forming a polymer mask on the substrate;

simultaneously etching the substrate as using the polymer mask and tailoring the polymer mask to form the plurality of stepped three-dimensional nano-structures, wherein the simultaneously etching the substrate as using the polymer mask and tailoring the polymer mask is performed in a reactive atmosphere consisting of chlorine gas, argon gas, and oxygen gas, the etching the substrate comprises chemical etching the substrate with chlorine gas, and the tailoring the polymer mask comprises chemical etching the polymer mask with oxygen gas;

removing the polymer mask; and depositing the metal layer on the substrate to cover the stepped three-dimensional nano-structures;

disposing single molecule samples on the metal layer; and detecting the single molecule samples using a Raman Spectroscopy system.

17. The method of claim 16, wherein the polymer mask is a monolayer nanosphere array and formed by the steps of:

preparing a nanosphere solution;

forming a monolayer nanosphere solution on the substrate; and drying the monolayer nanosphere solution.

18. The method of claim 16, wherein the polymer mask is a continuous film defining a plurality of holes arranged in arrays.

19. The method of claim 18, wherein the polymer mask is made of polymer and formed by nano-imprint or template deposition.

* * * * *